(12) United States Patent
Yanagawa et al.

(10) Patent No.: US 11,517,000 B2
(45) Date of Patent: Dec. 6, 2022

(54) METHOD OF STOPPING LARVA FROM SWIMMING OR CRAWLING

(75) Inventors: Toshiharu Yanagawa, Hiroshima (JP); Shinsuke Saito, Hyogo (JP); Keiji Yamashita, Hyogo (JP); Kyoko Kamiya, Hyogo (JP); Mai Nakagi, Hyogo (JP)

(73) Assignees: THE CHUGOKU ELECTRIC POWER CO., INC., Hiroshima (JP); SESSILE RESEARCH CORPORATION, Hyogo (JP)

( * ) Notice: Subject to any disclaimer, the term of this patent is extended or adjusted under 35 U.S.C. 154(b) by 909 days.

(21) Appl. No.: 14/421,203

(22) PCT Filed: Aug. 14, 2012

(86) PCT No.: PCT/JP2012/070700
§ 371 (c)(1),
(2), (4) Date: Jun. 24, 2015

(87) PCT Pub. No.: WO2014/027402
PCT Pub. Date: Feb. 20, 2014

(65) Prior Publication Data
US 2016/0143257 A1 May 26, 2016

(51) Int. Cl.
| | | |
|---|---|---|
| A01K 67/00 | (2006.01) | |
| A01K 67/033 | (2006.01) | |
| A01M 29/10 | (2011.01) | |
| C02F 1/30 | (2006.01) | |
| B08B 17/02 | (2006.01) | |

(52) U.S. Cl.
CPC .......... *A01K 67/033* (2013.01); *A01M 29/10* (2013.01); *B08B 17/02* (2013.01); *C02F 1/30* (2013.01); *C02F 2303/04* (2013.01)

(58) Field of Classification Search
CPC ...... A01K 67/033; A01M 21/10; A01M 21/04
USPC ......................................................... 119/238
See application file for complete search history.

(56) References Cited

U.S. PATENT DOCUMENTS

| | | | | | |
|---|---|---|---|---|---|
| 4,235,043 | A * | 11/1980 | Harasawa | ............ | A01G 9/1438 47/1.4 |
| 4,336,223 | A * | 6/1982 | Hillman | .................... | A61L 2/10 210/103 |
| 4,653,429 | A * | 3/1987 | Murphy | .................. | A23L 17/50 119/243 |
| 5,308,505 | A | 5/1994 | Titus et al. | | |
| 5,320,749 | A * | 6/1994 | Mullen | ....................... | A61L 2/10 210/199 |
| 5,655,483 | A * | 8/1997 | Lewis | .................. | A01M 19/00 119/720 |
| 6,447,720 | B1 * | 9/2002 | Horton, III | ............... | A61L 2/10 210/748.11 |
| 7,329,538 | B2 * | 2/2008 | Wainwright | ......... | G01N 33/579 435/23 |
| 7,473,008 | B2 * | 1/2009 | Crabb | .................... | C12M 21/02 362/101 |
| 7,695,675 | B2 * | 4/2010 | Kaiser | ....................... | A23L 3/28 210/319 |
| 8,240,312 | B2 * | 8/2012 | Feuerstein | ........... | A61N 5/0603 128/898 |
| 11,140,893 | B2 * | 10/2021 | Yanagawa | .................. | C02F 1/30 |
| 11,172,656 | B2 * | 11/2021 | Grajcar | ................... | A01K 29/00 |
| 2005/0147579 | A1 * | 7/2005 | Schneider | ............ | C09D 5/1687 424/78.09 |
| 2005/0232960 | A1 * | 10/2005 | Buccolini | ............... | C02F 1/008 424/405 |
| 2008/0206095 | A1 * | 8/2008 | Duthie | ....................... | A23L 3/28 422/24 |
| 2011/0226966 | A1 * | 9/2011 | Takahashi | ............... | A01K 63/04 250/492.1 |
| 2012/0006995 | A1 * | 1/2012 | Greuel | .................... | C02F 1/325 250/373 |
| 2013/0152864 | A1 * | 6/2013 | Grajcar | .................. | A01K 63/06 362/101 |

FOREIGN PATENT DOCUMENTS

| | | |
|---|---|---|
| JP | 5-228454 A | 9/1993 |
| JP | 07-037186 U | 7/1995 |
| JP | 8-164383 A | 6/1996 |
| JP | 11-196707 A | 7/1999 |
| JP | 11/278374 A | 10/1999 |
| JP | 2005-144213 A | 6/2005 |
| JP | 2010-187637 A | 9/2010 |
| WO | WO-98/30230 A1 | 7/1998 |

OTHER PUBLICATIONS

Second Office Action for Chinese Patent Application No. 201280075871. 9, dated Aug. 30, 2016 (English language translation provided) (10 pages).
Communication pursuant to Article 94(3) EPC for European Patent Application No. 12891404.1, dated Nov. 4, 2016 (5 pages).
Notice of Final Rejection for Korean Patent Application No. 10-2015-7005863, dated Dec. 27, 2016 (7 pages) (English language translation provided).
International Preliminary Report on Patentability for International Application No. PCT/JP2012/070700, dated Feb. 17, 2015 (6 pages).
English language translation of the Written Opinion of the International Searching Authority for International Application No. PCT/JP2012/070700, dated Nov. 20, 2012 (5 pages).
International Search Report for International Application No. PCT/JP2012/070700, dated Nov. 20, 2012 (2 pages).

(Continued)

*Primary Examiner* — Ebony E Evans
(74) *Attorney, Agent, or Firm* — Clark & Elbing LLP

(57) ABSTRACT

The present invention provides methods of stopping a larva of a sessile invertebrate in a settlement stage from swimming or crawling in water, by means of irradiating violet light having a wavelength range of 400 to 550 nm to the larva in the settlement stage of the sessile invertebrate.

10 Claims, No Drawings

(56) References Cited

OTHER PUBLICATIONS

Kobak, "Impact of light conditions on geotaxis behaviour of juvenile *Dreissena polymorpha*," Folia Malacologica 10(2):77-82 (2002).
Decision of Rejection for Chinese Patent Application No. 201280075871.9, dated Mar. 7, 2017 (8 pages) (English language translation provided).
Notification of Reexamination for Chinese Patent Application No. 201280075871.9, dated May 4, 2018 (Machine-generated English language translation provided) (8 pages).
"Mussel Culture Technology", edited and translated by Liu Anni, Wuzhou Publishing House, East Asian Book Company, p. 24, Sep. 1987 (Machine-generated English language translation provided) (3 pages).
"Mussel culture" edited by the Shandong Aquatic School Mariculture Research and Research Group, Agricultural Press, 1st Edition, pp. 49-51, Nov. 1978 (Machine-generated English language translation provided) (6 pages).
Zhang Fuzhen, "Observation of the habits of larvae and seedlings of purple mussels", Journal of Zoology, No. 3, pp. 129-130, 1963 (Machine-generated English language translation provided) (6 pages).

\* cited by examiner

METHOD OF STOPPING LARVA FROM SWIMMING OR CRAWLING

TECHNICAL FIELD

The present invention relates to methods of stopping larvae of sessile invertebrates in the settlement stage ("fuchaku-ki") from swimming or crawling in water.

BACKGROUND ART

In power plants, such as thermal or nuclear power plants, which use seawater as a coolant, marine invertebrates such as barnacles and bivalves including mussels are often settled inside of intake structures through which sea water is drawn from the sea and is supplied to condensers and outfall structures through which the sea water having passed through the condensers is discharged into the sea. An increased amount of settled marine invertebrates may possibly cause clogging of the coolant passages, resulting in a problem of, for example, reduction in cooling capacity. Accordingly, the settlement of marine invertebrates on the heat exchange systems is prevented by injecting a chlorine-based substance such as a sodium hypochlorite solution or chlorine dioxide into the coolant (Japanese Patent Laid-open Nos. 7-265867, 11-37666, 2005-144212, 2005-144213, and 2005-144214, and Japanese Patent No. 3605128). Other methods have also been developed which use a photocatalyst (Japanese Patent Laid-open No. 11-278374) or a laser beam (Japanese Patent Laid-open Nos. 2003-301435, 06-218367, and 08-164384).

SUMMARY OF THE INVENTION

An object of the present invention is to provide methods of stopping larvae of sessile invertebrates in the settlement stage from swimming or crawling in water.

One aspect of the present invention is a method of stopping a *Pteriomorphia* larva in a settlement stage from swimming or crawling in water, including the step of irradiating light in a wavelength range including 400 to 550 nm, preferably 400 to 440 nm, to the larva in the settlement stage. It is preferable that the light includes a part of the visible spectrum and does not include the entire visible spectrum. It is preferable that the light is not a laser beam. The water may be seawater. The sessile invertebrate may be a mussel or an oyster, and is preferably a pediveliger or a plantigrade of *Mytilus galloprovincialis* or *Perna viridis*.

EMBODIMENTS FOR CARRYING OUT THE INVENTION

The objects, features, advantages, and ideas of the present invention are apparent to those skilled in the art from consideration of the detailed description of this specification. Furthermore, those skilled in the art can easily reproduce the present invention from these descriptions. The mode and the specific example described below represent a preferable embodiment of the present invention, which is given for the purpose of illustration or description. The present invention is not limited thereto. It is obvious to those skilled in the art that various modifications may be made according to the descriptions of the present specification without departing from the spirit and scope of the present invention disclosed herein.

The method of stopping larvae of a sessile invertebrate in a settlement stage from swimming or crawling in water according to the present invention includes the step of irradiating light in a wavelength range including 400 to 440 nm to the larvae in the settlement stage. This is because irradiation of light having a wavelength range of 400 to 440 nm to the larvae in the settlement stage can cause the larvae in the settlement stage to close their shell.

Target sessile invertebrates are animals that drift in the sea in the early larval stage and then settle on an appropriate substrate during the larval settlement stage to metamorphose into adults. The sessile invertebrates include *Pteriomorphia*, in particular, mussels and oysters. The water used in this method is thus preferably seawater, but is not limited to the seawater. Instead, the water may be freshwater or salt water with a concentration different from seawater, such as a mixture of freshwater and seawater.

Mussel is a common name for bivalve molluscs in the family Mytilidae and includes, for example, Modiolinae such as *Modiolus nipponicus*, Lithophaginue such as *Lithophaga curta*, Crenellinae such as *Arvella manshurica* and *Musculista senhousia*, and Mytilinae such as *Mytilus coruscus*, *Limnoperna fortunei*, and *Mytilus galloprovincialis*. Oyster is a common name for molluscs in the family Ostreidue and includes, for example, Crassostrea such as *Crassostrea gigas* and *Crossostrea nippona* and Ostrea such as *Ostrea denselamellosa* and *Ostrea edulis*.

The target developmental stage is preferably the larval settlement stage. It is preferable that the larvae are pediveligers and plantigrades for the mussels and oysters, respectively, for example. This is because the present invention can prevent settlement of the larvae in the settlement stage onto a substrate. The substrate is not particularly limited and examples include seawater intake and outfall systems in power plants, coastal aquaculture facilities or fishery facilities.

The wavelength range of the light irradiated to the larvae in the settlement stage include 400 nm to 440 nm. For example, the light can include an ultraviolet radiation (having a wavelength range shorter than 400 nm), a visible radiation (of 400 to 830 nm) or an infrared radiation (having a wavelength range longer than 830 nm). It is preferable that the light is not a laser beam. It is also preferable that the light comprises a part of the visible spectrum and does not comprise the entire visible spectrum (e.g., 400 to 830 nm). More specifically, the wavelength range of the visible spectrum that can be used includes preferably a part of 400 to 830 nm (provided that the visible light with the entire visible spectrum (e.g., 400 to 830 nm) is excluded), and includes more preferably 400 to 750 nm, yet more preferably 400 to 620 nm, still more preferably 400 to 590 nm, yet further preferably 400 to 550 nm, still further preferably 400 to 495 nm, and most preferably 400 to 440 nm. In order to stop the larvae in the settlement stage from swimming or crawling in water, light only with the ultraviolet spectrum is not used because the violet light having a wavelength of 400 nm to 440 nm can be transmitted better through the seawater than the ultraviolet and thus can exert its effect over a wider area. The intensity and duration of the irradiation of the violet light of 400 nm to 440 nm are not specifically limited and can appropriately and easily be determined by those skilled in the art depending on the environment (e.g., quality, depth and clarity of the water) to be irradiated. The intensity of the irradiation is, however, preferably 200 to 2,000 W/m$^2$, more preferably 500 to 1,500 W/m$^2$ and most preferably 800 to 1,200 W/m$^2$. The time of the irradiation is preferably 1 second or longer, more preferably 6 seconds or longer, and most preferably 22 second or longer. The irradiation can be continuous or intermittent. In addition, no photocatalyst is used to stop larvae of a sessile invertebrate in the settlement stage from swimming or crawling in water, but a photocatalyst may be used to kill the larvae after they have been stopped from swimming or crawling using the light in a wavelength range including 400 to 440 nm.

The method of irradiation is not particularly limited, but a device such as an LED emitter, a mercury lamp, and a fluorescent tube may be used as an irradiator.

EXAMPLE

In this example, a pediveliger larva of *Mytilus galloprovincialis* was placed in each of Petri dishes containing 4 mL of seawater (depth of water: 2 mm) that had filtered through a filter with a mesh opening of 3 µm. Light having a wavelength range of 330 to 385 nm (U radiation), 400 to 440 nm (BV radiation), 460 to 490 nm (GFP radiation), or 510 to 550 nm (G radiation) was irradiated to the larva using an epifluorescence unit for a microscope (OLYMPUS SZX-RFL3) under the observation with a stereomicroscope. The irradiation was continued until the larva closed its shell. The irradiation time before the shell closure and the duration of time while the larva kept its shell closed after the irradiation was stopped were measured. If the larva did not close its shell after 10 minutes, the irradiation was stopped at that time. A plurality of the tests was performed for each range of the wavelength using seven larvae. The conditions and results of the tests are given in Table 1 below.

TABLE 1

Seven pediveligers of *Mytilus galloprovincialis*

| Irradiation | Wavelength range (nm) | Intensity W/m² | Average irradiation time (sec.) | Average shell closure time (sec.) |
|---|---|---|---|---|
| U | 330-385 | 56.2 | 67 | 87 |
| BV | 400-440 | 1013.0 | 22 | 120 |
| GFP | 460-490 | 418.2 | Not closed | — |
| G | 510-550 | 1875.7 | Not closed | — |

Not closed: the larva did not close its shell after the lapse of 10 minutes.

Similar tests were performed on pediveligers and plantigrades of *Perna viridis* and the conditions and results of the tests are given in Tables 2 and 3.

TABLE 2

Eleven pediveligers of *Perna viridis*

| Irradiation | Wavelength range (nm) | Intensity W/m² | Average irradiation time (sec.) | Average shell closure time (sec.) |
|---|---|---|---|---|
| U | 330-385 | 56.2 | 17 | 174 |
| BV | 400-440 | 1013.0 | 10 | 304 |
| GFP | 460-490 | 418.2 | Not closed | — |
| G | 510-550 | 1875.7 | Not closed | — |

TABLE 3

Six plantigrades of *Perna viridis*

| Irradiation | Wavelength range (nm) | Intensity W/m² | Average irradiation time (sec.) | Average shell closure time (sec.) |
|---|---|---|---|---|
| U | 330-385 | 56.2 | 16 | 61 |
| BV | 400-440 | 1013.0 | 5 | 134 |
| GFP | 460-490 | 418.2 | 48 | 53 |
| G | 510-550 | 1875.7 | 26 | 67 |

The pediveligers with U and BV irradiations and the plantigraedes with any one of the irradiation ranges tested closed their shells and stopped swimming or crawling during the irradiation of the light. The larvae kept closing their shells for a certain duration of time after the irradiation was stopped. Considering that the violet light has a higher transmittance in the seawater than the ultraviolet light, it can be understood that the BV irradiation for the pediveligers and the BV, GFP and G irradiations for the plantigrades are particularly effective in order to stop the larvae in the settlement stage from swimming or crawling in water.

INDUSTRIAL APPLICABILITY

The present invention makes it possible to provide methods of stopping larvae of sessile invertebrates in the settlement stage from swimming or crawling in water.

The invention claimed is:

1. A method of stopping a larva of *Pteriomorphia* in a settlement stage from swimming or crawling in water, comprising the step of:
    irradiating light in a wavelength range including 400 to 550 nm to the larva in the settlement stage, wherein the light consists of a part of the visible spectrum and does not comprise the entire visible spectrum and wherein the light is not a laser beam.

2. A method of stopping a larva of *Pteriomorphia* in a settlement stage from swimming or crawling in water, comprising the step of:
    irradiating light in a wavelength range including 400 to 440 nm to the larva in the settlement stage, wherein the light consists of a part of the visible spectrum and does not comprise the entire visible spectrum and wherein the light is not a laser beam.

3. The method according to claim 1 or 2, wherein the water is seawater.

4. The method according to claim 3, wherein the sessile invertebrate is a mussel or an oyster.

5. The method according to claim 4, wherein the larva in the settlement stage is a pediveliger or a plantigrade of *Mytilus galloprovincialis* or *Perna viridis*.

6. The method according to claim 3, wherein the larva in the settlement stage is a pediveliger or a plantigrade of *Mytilus galloprovincialis* or *Perna viridis*.

7. The method according to claim 1 or 2, wherein the sessile invertebrate is a mussel or an oyster.

8. The method according to claim 7, wherein the larva in the settlement stage is a pediveliger or a plantigrade of *Mytilus galloprovincialis* or *Perna viridis*.

9. The method according to claim 1 or 2, wherein the larva in the settlement stage is a pediveliger or a plantigrade of *Mytilus galloprovincialis* or *Perna viridis*.

10. The method according to claim 1 or 2, wherein the intensity of the irradiated light is 200 to 2,000 W/m².

* * * * *